United States Patent [19]

Frazier

[11] 4,297,348

[45] Oct. 27, 1981

[54] COMPOSITION AND METHOD FOR THE TREATMENT OF ACNE

[75] Inventor: Stephen E. Frazier, Orlando, Fla.

[73] Assignee: Rush-Hampton Industries, Inc., Longwood, Fla.

[21] Appl. No.: 139,208

[22] Filed: Apr. 11, 1980

[51] Int. Cl.$^3$ ............................................. A61K 31/70
[52] U.S. Cl. ...................................... 424/180; 536/8; 424/343
[58] Field of Search .................... 424/180, 343; 536/1, 536/4, 8

[56] References Cited

U.S. PATENT DOCUMENTS

| | | | |
|---|---|---|---|
| 2,786,832 | 3/1957 | Wender et al. | 536/8 |
| 3,530,217 | 9/1970 | White et al. | 424/180 |
| 3,535,422 | 10/1970 | Cox et al. | 424/164 |
| 4,052,515 | 10/1977 | McDermott et al. | 424/343 |
| 4,056,611 | 11/1977 | Young | 424/62 |

OTHER PUBLICATIONS

Kefford et al., The Chemical Constituents of Citrus Fruit, p. 146, Academic Press, New York, 1970.

Primary Examiner—Johnnie R. Brown
Assistant Examiner—Blondel Hazel
Attorney, Agent, or Firm—Finnegan, Henderson, Farabow, Garrett & Dunner

[57] ABSTRACT

Therapeutic compositions for the treatment of acne which comprise from about 0.1% to about 5% by weight naringin, from about 0.1% to about 10% by weight naringenin, from about 0.05% to about 5% by weight of an antimicrobially active partially hydrolyzed naringin, from about 0.01% to about 5% weight colloidal silica, and from about 80% to 97% by weight of a solvent.

8 Claims, No Drawings

COMPOSITION AND METHOD FOR THE TREATMENT OF ACNE

BACKGROUND OF THE INVENTION

This invention relates to a novel therapeutic composition for the treatment of acne and to a method of using such compositions.

Acne is a skin disorder characterized by an excessive flow of sebum, or skin oil, from the sebaceous glands. Sebum reaches the surface of the skin through the duct of the hair follicle. Excessive amounts of sebum in the duct and on the skin acts to block the continuous flow of sebum, thus producing a thickening of the sebum which eventually becomes a solid plug. As a result, a papule, pustule, or cyst often forms, usually contaminated with bacteria which causes secondary infections.

Prior art topical therapeutic agents have attempted to prevent blockage of the follicular duct, reopen the duct once it has become blocked, act against the infecting bacteria or thickened sebum, or provide combinations of each of these actions.

Unfortunately, the prior art topical therapeutic compositions for the treatment of acne generally remove at least one layer of a user's skin. Accordingly, workers in the art have sought therapeutically effective compositions for the treatment of acne which do not remove the skin of the user.

The present invention is directed to therapeutic compositions which, when topically applied to the skin, provide an effective treatment for acne without skin removal. The active agents in these compositions are derived from natural food sources. Advantageously, these compositions, which dry to a white powdery residue, are non-sticky, non-toxic and otherwise safe for use.

SUMMARY OF THE INVENTION

The present invention provides therapeutically effective compositions for the treatment of acne. These compositions comprise:
a. from about 0.1% to about 5% by weight naringin;
b. from about 0.1% to about 10% by weight naringenin;
c. from about 0.05% to about 5% by weight of an antimicrobially active partially hydrolyzed naringin; and
d. from about 80% to about 98% by weight of a solvent. Preferably, the compositions also include from about 0.01% to about 5% by weight colloidal silica.

A preferred range for the compositions within the present invention comprises: from about 0.5% to about 3% by weight naringin; from about 1% to about 5% by weight naringenin; from about 0.1% to about 2.5% by weight of an antimicrobially active partially hydrolyzed naringin; and from about 87.5% to about 97% by weight of a solvent. The preferred range of colloidal silica is from about 0.1% to about 2% by weight.

A particularly preferred composition comprises about 1% by weight naringin; about 3.5% by weight naringenin; about 0.5% by weight of an antimicrobially active partially hydrolyzed naringin; about 0.25% by weight colloidal silica; and about 94.75% by weight isopropyl alcohol.

The invention also pertains to a method of treating acne comprising topically applying to the skin the aforementioned compositions in an amount effective to treat acne.

DETAILED DESCRIPTION OF THE INVENTION

One of the components of the compositions of the present invention, naringin, is a known natural plant flavanoid glycoside. It has the structure

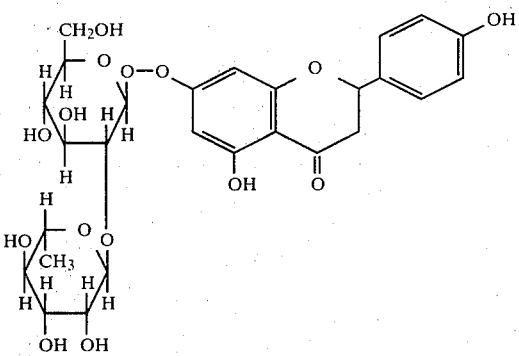

Naringenin, another component of the compositions of the present invention, having the formula

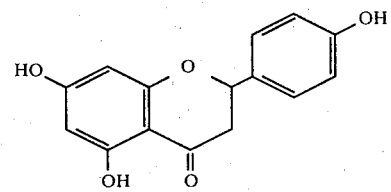

is a known flavanoid aglycone which can be prepared by the acid hydrolysis of naringin.

The naringenin used in the present compositions can be prepared from naringin by techniques known in the art. Specifically, an aqueous solution of hydrochloric acid can be added to naringin, and the mixture stirred and refluxed. Preferably, 0.5 N hydrochloric acid is used. After the solution is cooled, the yellow solid product is filtered and washed with water until the washings are no longer acidic.

In my copending application, U.S. Patent application Ser. No. 06/058,810, filed July 19, 1979 issued on Dec. 9, 1980 as U.S. Pat. No. 4,238,483, for ANTIMICROBIAL COMPOSITIONS OF MATTER AND A PROCESS FOR PREPARING ANTIMICROBIAL COMPOSITIONS OF MATTER FROM NATURALLY OCCURRING FLAVANOID GLYCOSIDES, which is incorporated herein by reference, I have disclosed and claimed, inter alia, a novel composition of matter which I have denominated as partially hydrolyzed naringin. The partially hydrolyzed naringin used in the present invention is prepared in accordance with the procedure described in the aforementioned copending application.

As explained in Examples 6 and 7 of my copending Application, the partially hydrolyzed naringin contains two components designated as $F_1$ and $F_2$, which each differ from both naringin and naringenin. Although neither $F_1$ nor $F_2$ alone possesses significant antimicrobial activity when tested by conventional agar plate screening tests, mixtures of $F_1$ and $F_2$ surprisingly do possess significant antimicrobial activity. Although $F_2$ is not completely water soluble, it is more water soluble than naringenin. Further, $F_1$ increases the water solubility of $F_2$.

As described in the above-noted application, acid hydrolysis of naringin is carried out under substantially quiescent conditions, with agitation being avoided. The reaction is allowed to proceed long enough to hydrolyze naringin to an intermediate composition having antimicrobial activity, i.e., to the partially hydrolyzed naringen. The specific length of time the reaction should be permitted to proceed depends, of course, on a number of factors, such as the particular reactants and particular reaction conditions employed.

If the reaction is allowed to proceed too long, the insoluble antimicrobial composition will be converted to naringenin. Although the antimicrobial activity of naringenin has been the subject of scientific controversy, I have now discovered that naringenin is in fact antimicrobially active. Its water solubility and cellular diffusiveness, factors which contribute to degree of antimicrobial activity, are, however, less than those of partially hydrolyzed naringin.

In order to avoid conversion of partially hydrolyzed naringin to naringenin, it is preferred that the hydrolysis mixture be transferred to an ice water bath after completion of the desired degree of hydrolysis. The partially hydrolyzed naringin may be isolated by using such well-known steps as filtering, washing, and drying.

As should be apparent, the degree of hydrolysis of the partially hydrolyzed naringin can vary. So long as the partially hydrolyzed naringin exhibits antimicrobial activity, it can be used in the present invention. By functioning as an antimicrobial agent, the partially hydrolyzed naringin acts to inhibit the excessive bacterial growth associated with acne.

Various solvents can be used in the present invention, such as alkyl alcohols having from 1 to 6 carbon atoms, e.g., methanol, ethyl alcohol, propyl alcohol and butyl alcohol. Isopropyl alcohol is a particularly preferred solvent. Other suitable solvents include acetone, water and a mixture of a saturated or unsaturated higher alcohol having from 6 to 12 carbon atoms and a lower alcohol having 2 or 3 carbon atoms. The higher alcohol can be a primary or secondary alcohol. Preferably, the higher alcohol is a saturated primary alcohol. Examples of suitable higher alcohols include the following: 1-hexanol, 1-heptanol, 1-octanol, 1-nonanol, 1-decanol, 1-dodecanol, 2-octanol, 2-decanol, 4-octanol, 5-nonanol, 3-hexen-1-ol, 3-decen-1-ol, and 9-decen-1-ol.

While compositions comprising naringin, naringenin, partially hydrolyzed naringin, and a solvent provide an effective treatment for acne, it has been discovered that the addition of colloidal silica to the composition results in more rapid healing. A particularly suitable formulation of colloidal silica is sold under the trademark Syloid 244 by W. R. Grace. The colloidal silica functions as a drying and abrasive agent. By acting to remove excess keratin and sebum, the colloidal silica helps prevent the blockage of the follicular duct.

Further, use of colloidal silica in the compositions of the present invention results in formation on drying of a white powdery residue. For those utilizing make-up, this powdery residue serves as a make-up base, which inhibits the reoccurrence of acne.

The invention will be further explained by reference to the following examples. These examples, which are not limiting, include preferred embodiments of the present invention. In the following examples, unless otherwise specified, all percentages are by weight.

EXAMPLE 1

616.5 grams naringin were added to a round bottomed flask, followed by the addition of about one liter of 0.5 N hydrochloric acid. Upon stirring and refluxing, the naringin dissolves to form a yellow to red-brown solution. While a brown gummy or oily material initially forms, it eventually disappears. As the reaction proceeds, a yellow solid precipitates. The reaction time is approximately 2 to 4 hours. The solution is cooled, and the yellow solid filtered and washed with copious amounts of water until the washings are no longer acidic. The amount of naringenin produced is about 160 grams.

EXAMPLE 2

Eight test-tubes were prepared, each containing 1 gram of naringin (obtained from Sunkist Corporation) and 15 ml of 0.5 molar HCl. The tubes were initially placed in a hot water bath, at approximately 100° C. None of the solutions in the tubes were stirred or agitated in any way during the heat treatment. In order to "freeze-out" or immediately stop the reaction, the tubes were transferred at different times to an ice water bath.

| Tube Number | Time in Hot Water Bath (min.) |
|---|---|
| 1 | 30 |
| 2 | 60 |
| 3 | 90 |
| 4 | 120 |
| 5 | 150 |
| 6 | 180 |
| 7 | 220 |
| 8 | 240 |

Although the tube 1 solution, when removed, was clear, a gummy precipitate formed when the tube was cooled. After thirty-five minutes a precipitate began forming in all the remaining tubes. An oil, which began forming at the top of all tubes after forty minutes, moved to the bottom of each tube within five additional minutes.

At 80 minutes, all remaining solutions were clear, with the oily, active precipitate still at the bottom. At 100 minutes, the oil began to disappear and crystals began growing from the oil layer, while, at about the same time, a layer of clear, light yellow crystals began forming near the top of the solutions.

The precipitates were filtered out from tubes 1–8 and washed with about 150 ml of distilled $H_2O$ to substantially remove all remaining acid. After washing, the precipitates were vacuum dried in an oven at about 50° C. for about two hours.

To ascertain the antimicrobial activity of the dried samples, they were pulverized and 10.0 mg of each were weighed into small test tubes. After dissolution in 10.0 ml of spectrophotometric grade acetone, each sample was pipetted onto a separate, sterile, dry, 6 mm diameter, filter paper disc. After allowing for evaporation at about 50° C., the pipetting and drying steps were subsequently repeated until each 10.0 mg sample was completely transferred to a disc.

The discs, when dry, were each applied to the surface of a 150×15 mm Trypticase Soy Agar petri-dish, previously swabbed, following the Kirby-Bauer technique, with a suspension of *S. aureus* ATCC 6538. Great care was taken to place the sample-containing surface of each prepared disc in contact with the bacteria. After 60 minutes at room temperature, the petri-dishes were incubated at 37° C. for 18 hours.

Inhibition zone diameters were measured four times to the nearest estimated 0.1 mm with a clean rule. The results appear in Table I.

TABLE I

| Test Tube Sample | Solvent to Dissolve | Inhibition Zones (mm) versus *S. aureus* ATCC 6538 (including diameter of the disc) | Inhibition Zone Mean X |
|---|---|---|---|
| 1 | Acetone | 10.0, 9.8, 10.0, 9.7 | 9.9 |
| 2 | Acetone | 12.0, 12.0, 12.0, 12.0, | 12.0 |
| 3 | Acetone | 10.0, 9.8, 9.8, 10.0 | 9.9 |
| 4 | Acetone | 9.8, 10.0, 9.5, 9.8 | 9.8 |
| 5 | Acetone | 8.5, 8.5, 8.3, 8.5 | 8.4 |
| 6 | Acetone | 8.0, 7.9, 7.8, 7.8 | 7.9 |
| 7 | Acetone | 7.0, 7.0, 6.8, 7.0 | 7.0 |
| 8 | Acetone | 7.0, 7.2, 7.0, 7.0 | 7.0 |
| blank disc | none | no zone | — |

In this example of the hydrolysis of naringin, the level of antimicrobial activity of the partial hydrolysis products varied with reaction time, reaching a maximum at about 60 minutes.

EXAMPLE 3

In order to quantify the ability of the component, naringenin, to inhibit the growth of skin bacteria encountered in acne lesions, the substance was tested against *Staphylococcus aureus* ATCC 6538. Solutions of naringenin in 10 ml AATCC broth were prepared in which the naringenin concentration was 150 ppm, 200 ppm, 300 ppm, 400 ppm and 500 ppm. Three solutions of each concentration were used. Each tube was inoculated with a loop full of the test organism and incubated at 37° C. under aerobic conditions for seven days. Examination of the tubes showed that the minimum concentration of naringenin necessary to inhibit the growth of *Staphylococcus aureus* ATCC 6538 lies between 150 ppm and 200 ppm.

EXAMPLE 4

The antimicrobial activity of naringenin was demonstrated using *Staphylococcus aureus* ATCC 25923, a bacterium encountered in acne lesions, using the procedure described in Example 3. Solutions of naringenin in 10 ml AATCC broth were prepared in which the naringenin concentration was 100 ppm, 200 ppm, 300 ppm, and 400 ppm. Three solutions of each concentration were used. Each tube was inoculated with a loop full of the test organism and incubated at 37° C. under aerobic conditions for 7 days. Examination of the tubes showed that the minimum concentration of naringenin necessary to inhibit the growth of *Staphlococcus aureus* ATCC 25923 lies between 100 and 200 ppm.

EXAMPLE 5

The antimicrobial activity of naringenin was demonstrated using *Propionibacterium acnes* ATCC 6916, a bacterium encountered in acne lesions, using a procedure similar to Example 3. Solutions of naringenin and 10 ml Actinomyces broth were prepared in which the concentration of naringenin was 50 ppm, 100 ppm, 200 ppm, 300 ppm, and 400 ppm. Three solutions of each concentration were used. Each tube was inoculated with a loop full of the test organism and incubated at 37° C. for 7 days in an anaerobic jar in an atmosphere of hydrogen and carbon dioxide. Examination of the tubes showed that the minimum concentration of naringenin necessary to inhibit the growth of *Propionibacterium acnes* ATCC 6916 lies between 100 and 200 ppm.

EXAMPLE 6

The fungicidal activity of naringenin was demonstrated using *Pityrosporum ovale* ATCC 14521, a fungus encountered in acne lesions. This organism is cultured in a corn oil medium prepared with Sabouraud Dextrose broth and Mazola ® Corn Oil. Solutions of naringenin and this broth were made in which the concentration of naringenin in the upper oil layer was 200 ppm, 400 ppm, 600 ppm, and 800 ppm. Three solutions of each concentration were tested. Each tube was inoculated with a loop full of the test organism and incubated at 37° C. under aerobic conditions for 7 days. Examination of the tubes showed that naringenin in concentrations of 200 ppm or greater severely retarded the growth of *Pityrosporum ovale* ATCC 14521.

EXAMPLE 7

Nine compositions were prepared (denominated A through I) by dissolving, in various combinations, naringin, naringenin, partially hydrolyzed naringin, and colloidal silica, in an aqueous solution of 70% isopropyl alcohol. The partially hydrolyzed naringin that was used corresponds to that produced in Tube Number 2 of Example 2. The following table summarizes the various compositions that were prepared.

TABLE II

|  | A | B | C | D | E | F | G | H | I |
|---|---|---|---|---|---|---|---|---|---|
| Naringin | 240 mg (2.39%) | 450 mg (4.50%) | 0 (0%) | 250 mg (2.50%) | 100 mg (1.00%) | 350 mg (3.50%) | 100 mg (1.00%) | 350 mg (3.49%) | 0 (0%) |
| Naringenin | 240 mg (2.39%) | 0 (0%) | 450 mg (4.50%) | 250 mg (2.50%) | 350 mg (3.50%) | 100 mg (1.00%) | 350 mg (3.49%) | 100 mg (1.00%) | 0 (0%) |
| Partially Hydrolyzed Naringin | 50 mg (0.50%) | 50 mg (0.50%) | 50 mg (0.50%) | 0 (0%) | 50 mg (0.50%) | 50 mg (0.50%) | 50 mg (0.50%) | 50 mg (0.50%) | 0 (0%) |
| Solvent | 9.5 g (94.72%) | 9.5 g (95.00%) | 9.5 g (95.00%) | 9.5 g (95.00%) | 9.5 g (95.00%) | 9.5 g (95.00%) | 9.5 g (94.76%) | 9.5 g (94.76%) | 9.5 g (99.74%) |
| Colloidal Silica | 0 (0%) | 0 (0%) | 0 (0%) | 0 (0%) | 0 (0%) | 0 (0%) | 25 mg (0.25%) | 25 mg (0.25%) | 25 mg (0.26%) |

In compositions G and I, the colloidal silica used was Syloid 244, in composition H, the colloidal silica used was Zeofree 80, made by J. M. Huber Corp. of Havre de Grace, Md. Each composition was tested on one human female, with the exception of composition G, which was tested on three human females. Each composition was used once a day for one or two days. Although each of the compositions A, E, F, G and H inhibited acne, the best results were obtained with compositions E and G.

What is claimed is:

1. A therapeutic composition for the treatment of acne comprising:
   a. from about 0.1% to about 5% by weight naringin;
   b. from about 0.1% to about 10% by weight naringenin;
   c. from about 0.05% to about 5% by weight of an antimicrobially active partially hydrolyzed naringin; and
   d. from about 80% to about 98% by weight of a suitable solvent.

2. The composition of claim 1 comprising, in addition, from about 0.01% to about 5% by weight colloidal silica.

3. The composition of claim 1 comprising from about 0.5% to about 3% by weight naringin; from about 1% to about 5% by weight naringenin; from about 0.1% to about 2.5% by weight of an antimicrobially active partially hydrolyzed naringin; and from about 87.5% to about 97% of a solvent.

4. The composition of claim 3 comprising, in addition, from about 0.1% to about 2% by weight collodial silica.

5. The composition of claims 1, 2, 3, or 4 wherein the solvent is an alkyl alcohol having from 1 to 6 carbon atoms.

6. The composition of claim 5 wherein the solvent is isopropyl alcohol.

7. A therapeutic composition for the treatment of acne comprising: about 1% by weight naringin; about 3.5% by weight naringenin; about 0.5% by weight of an antimicrobially active partially hydrolyzed naringin; about 0.25% by weight colloidal silica; and about 94.75% by weight isopropyl alcohol.

8. A method for the treatment of acne in humans comprising topically applying an amount effective to treat acne of the composition of any one of claims 1, 2, 3, 4 or 7.

* * * * *